United States Patent [19]
Verstrat et al.

[11] Patent Number: 5,840,789
[45] Date of Patent: Nov. 24, 1998

[54] AQUEOUS COMPOSITIONS THICKENED WITH ACRYLATE-BASED POLYMERIC RHEOLOGY MODIFIERS

[75] Inventors: Daniel W. Verstrat, Ooltewah; Milagros C. Barron, Hixson, both of Tenn.

[73] Assignee: National Starch and Chemical Investment Holding Corporation, Wilmington, Del.

[21] Appl. No.: 910,378

[22] Filed: Aug. 13, 1997

Related U.S. Application Data

[63] Continuation-in-part of Ser. No. 698,690, Aug. 16, 1996.
[51] Int. Cl.$^6$ ........................................................ C08K 5/41
[52] U.S. Cl. ...................... 524/156; 524/140; 524/147; 524/157; 524/161; 524/284; 524/300; 524/320; 524/321; 524/366; 524/376; 524/378; 524/401; 524/417; 524/419
[58] Field of Search ..................................... 524/320, 321, 524/156, 157, 140, 147, 161, 284, 300, 376, 378, 366, 401, 419, 417

[56] References Cited

U.S. PATENT DOCUMENTS

| | | | |
|---|---|---|---|
| Re. 33,156 | 1/1990 | Shay et al. | 526/301 |
| 4,012,437 | 3/1977 | Shachat et al. | 260/482 R |
| 4,128,520 | 12/1978 | Barabas et al. | 260/29.7 W |
| 4,616,074 | 10/1986 | Ruffner | 526/318 |
| 4,806,345 | 2/1989 | Bhattacharyya | 424/70 |
| 4,892,916 | 1/1990 | Hawe et al. | 526/304 |
| 5,011,987 | 4/1991 | Barron et al. | 560/221 |
| 5,100,660 | 3/1992 | Hawe et al. | 424/78.35 |
| 5,164,177 | 11/1992 | Bhatt et al. | 424/47 |
| 5,238,992 | 8/1993 | Outubuddin | 524/710 |
| 5,294,692 | 3/1994 | Barron et al. | 526/301 |

FOREIGN PATENT DOCUMENTS

| | | |
|---|---|---|
| 190892 B1 | 8/1986 | European Pat. Off. . |
| 0 329 419 A2 | 8/1989 | European Pat. Off. . |
| 0 398 576 B1 | 11/1990 | European Pat. Off. . |
| 49-5512 | 7/1974 | Japan . |

OTHER PUBLICATIONS

J. A. Wenninger & G. N. McEwen, "International Cosmetic Ingredient Handbook", Third Edition, 1995.
K. G. Srinivasan and D. L. Neumann, "Cationic acrylic latex as paper saturants", Sep. 1986 Tappi Journal, pp. 104–106.
J. A. Wenninger & G. N. McEwen, "International Cosmetic Ingredient Handbook", Sixth Edition, 1995.

*Primary Examiner*—Judy M. Reddick
*Attorney, Agent, or Firm*—John D. Thallemer

[57] ABSTRACT

The present invention relates to aqueous compositions having pH of less than or equal to about 11 and which contain a thickening amount of an acrylate-based rheology modifier, which modifier contains an emulsion which is prepared by single-stage emulsion polymerization of a $C_2$–$C_6$ alkyl ester of acrylic acid and/or a $C_1$–$C_6$ alkyl ester of methacrylic acid, a monomer chosen from a vinyl-substituted heterocyclic compound containing at least one of a nitrogen or sulfur atom, (meth)acrylamide, a mono- or di-($C_1$–$C_4$)alkylamino ($C_1$–$C_4$)alkyl (meth)acrylate, a mono or di-($C_1$–$C_4$) alkylamino ($C_1$–$C_4$)alkyl (meth)acrylamide, and optionally cross-linking monomers and/or associative monomers, in the presence of water, a first surfactant, a free-radical initiator and an alcohol selected from $C_2$–$C_{12}$ linear or branched alcohols, ethylene glycol, propylene glycol and glycerol, or mixtures thereof, and essentially in the absence of a polymeric colloidal stabilizer such as polyvinyl alcohol, and which compositions further contain an active ingredient selected from the group consisting of an acid and a second surfactant which may be the same as or different than the first surfactant.

11 Claims, No Drawings

AQUEOUS COMPOSITIONS THICKENED WITH ACRYLATE-BASED POLYMERIC RHEOLOGY MODIFIERS

This is a continuation-in-part application of pending U.S. patent application Ser. No. 08/698,690, filed on Aug. 16, 1996 pending.

FIELD OF THE INVENTION

The present invention is related to acid- and/or surfactant-containing aqueous compositions having pH of less or equal to about 11, more particularly from about 0.4 to about 10.5, which have been thickened with an acrylate-based polymeric rheology modifier.

BACKGROUND OF THE INVENTION

Rheology modifiers are used generally to adjust or modify the rheological properties of aqueous compositions. Such properties include, without limitation, viscosity, flow rate, stability to viscosity change over time, and the ability to suspend particles in such aqueous compositions. The particular type of modifier used will depend on the particular aqueous composition to be modified and on the particular end-use of that modified aqueous composition. Examples of conventional rheology modifiers include thickeners such as cellulosic derivatives, polyvinyl alcohol, sodium polyacrylate, and other water-soluble macromolecules, and copolymeric emulsions in which monomers with acid groups have been introduced onto the main chain. Such thickeners are used widely in fiber treatment and adhesives.

It has been reported that when thickeners such as cellulosic derivatives and polyvinyl alcohol are mixed with aqueous emulsions, the thickened emulsion tends to exhibit poor stability to viscosity change over time. The cellulosics are said to result in a substantial decline in viscosity over time. It also has been reported that large quantities of polyvinyl alcohol are required in order to thicken aqueous emulsions. When such thickened aqueous emulsions are used in, for example, adhesives and coatings, the high levels of polyvinyl alcohol result in a loss of adhesive and/or cohesive properties as well as a loss in water resistance in the films formed therefrom.

Another class of rheology modifiers known to thicken aqueous emulsions is one typically referred to as associative modifiers. Such associative modifiers are reported in U.S. Pat. Nos. 4,743,698, 4,600,761, U.S. Pat. No. RE 33,156, U.S. Pat. Nos. 4,792,343, 4,384,096, 3,657,175, 5,102,936 and 5,294,692. As noted, these thickeners become effective upon the addition of base, thereby raising the pH of the thickened composition to alkaline, but the thickeners are not designed to thicken aqueous compositions having a pH less than 7.

Other rheology modifiers which are "activated" by the addition of acid to aqueous compositions which contain the modifiers also have been reported. As reported, emulsions are prepared via free-radical emulsion polymerization utilizing colloidal stabilizers. The emulsions are mixed with the composition to be thickened and then acid is added to the mix, thereby lowering the pH of the system to 6.5 to 0.5. These thickeners are reported to be effective at thickening certain acidic aqueous compositions, but are not effective at thickening aqueous compositions having basic pH.

It would be desirable to develop a rheology modifier which is stable to change in viscosity and phase separation over time, which does not detrimentally affect film properties such as adhesive/cohesive properties and water resistance, and which advantageously may be used to thicken both acidic and basic aqueous compositions.

SUMMARY OF THE INVENTION

The present invention relates to thickened aqueous compositions which have a pH of less than or equal to about 11, preferably from about 0.4 to about 10.5, which compositions comprise a thickening amount of an acrylate-based polymeric rheology modifier in the form of a stable, aqueous emulsion; and an active ingredient selected from the group consisting of an acid and a surfactant, said active ingredient being present in amounts effective to provide to said thickened composition the performance characteristics required for the particular end-use thereof. The stable emulsion of the acrylate-based polymeric rheology modifier is prepared by single-stage emulsion polymerization of from about 5 to about 80 weight percent of an acrylate monomer (a) selected from the group consisting of a $C_2$–$C_6$ alkyl ester of acrylic acid and a $C_1$–$C_6$ alkyl ester of methacrylic acid, from about 5 to about 80 weight percent of a monomer (b) selected from the group consisting of a vinyl-substituted heterocyclic compound containing at least one of a nitrogen or sulfur atom, (meth)acrylamide, a mono- or di-($C_1$–$C_4$)alkylamino ($C_1$–$C_4$)alkyl (meth)acrylate, a mono or di-($C_1$–$C_4$) alkylamino ($C_1$–$C_4$)alkyl (meth)acrylamide, 0 to about 2 weight percent of a cross-linking monomer (c); and 0 to about 30 weight percent of an associative monomer (d), all percentages based on the total weight of monomer. The emulsion polymerization is conducted in the presence of water, a first surfactant in amounts effective to emulsify the polymer in the water, a free-radical initiator, and from about 0.5 to about 20 weight percent of an alcohol selected from the group consisting of a $C_2$–$C_{12}$ linear or branched monohydric alcohol and non-polymeric polyhydric alcohols, such as ethylene glycol, propylene glycol and glycerol, based on the total weight of the stable emulsion. The emulsion polymerization is conducted essentially in the absence of a polymeric colloidal stabilizer.

DETAILED DESCRIPTION OF THE INVENTION

Exemplary thickened aqueous compositions of the present invention include, without limitation, cleansers such as toilet bowl cleaners, hard surface cleaners and liquid hand dishwashing detergents, drilling fluid additives, saturants for corrugated paper manufacture, adhesives, paints, inks, dyes and anti-stat coatings for paper. The emulsions are stable, meaning that no appreciable phase separation or change in viscosity is noted over time, for example one to five days at standard temperature and pressure, such that the emulsions may not be used to thicken aqueous compositions having pH of less than or equal to about 11.

The acrylate monomers (a) are selected from the group consisting of esters prepared from acrylic acid and $C_2$–$C_6$ alcohols, such as ethyl or propyl alcohol, and esters prepared from methacrylic acid and $C_1$–$C_6$ alcohols. (Meth)acrylic acid is used herein to denote both acrylic acid and methacrylic acid. Preferred acrylate monomers comprise $C_2$–$C_6$ alkyl esters of acrylic acid. Even more preferred, the acrylate monomer is ethyl acrylate. From about 5 to about 80 weight percent of the acrylate monomer are used in preparing the composition of the present invention, based on total weight of monomer. Preferably from about 15 to about 70 weight percent of the acrylate monomer are used, based on total weight of monomer. More preferably, from about 40 to about 70 weight percent of the acrylate monomer are used.

Methyl acrylate should not be used in preparing the emulsions and is not included within the metes and bounds of this invention, as it has been found to result in emulsions which are unstable with respect to viscosity change over time. It was unexpected that polymers prepared in the absence of a polymeric colloidal stabilizer with ethyl acrylate provided stability to viscosity change over time when compared to polymers prepared in the absence of a polymeric colloidal stabilizer with methyl acrylate, as emulsions prepared with methyl acrylate were found to be unstable to viscosity change.

In addition to the acrylate ester (a), polymerized therewith is a monomer (b) selected from the group consisting of a vinyl-substituted heterocyclic compound containing at least one of a nitrogen or sulfur atom, (meth)acrylamide, a mono- or di-($C_1$–$C_4$)alkylamino ($C_1$–$C_4$)alkyl (meth)acrylate, a mono or di-($C_1$–$C_4$)alkylamino ($C_1$–$C_4$)alkyl (meth)acrylamide. Exemplary monomers include N,N-dimethylamino ethyl methacrylate, N,N-diethylamino ethyl acrylate, N,N-diethylamino ethyl methacrylate, N-t-butylamino ethyl acrylate, N-t-butylamino ethyl methacrylate, N,N-dimethylamino propyl acrylamide, N,N-dimethylamino propyl methacrylamide, N,N-diethylamino propyl acrylamide and N,N-diethylamino propyl methacrylamide. From about 5 to about 80 weight percent of the monomer are used in preparing the modifiers of the present invention, based on total weight of monomer. Preferably, from about 10 to about 70 weight percent of the monomer are used, based on total weight of monomer. More preferably, from about 20 to about 60 weight percent of the monomer are used.

In addition to the required monomers, monomers which provide cross-linking in the polymer may also be utilized in relatively low amounts, up to about 3 weight percent, based on the total weight of monomer. When used, the cross-linking monomers preferably are used at levels of from about 0.1 to about 3 weight percent, based on total weight of monomer. Cross-linking monomers include multi-vinyl-substituted aromatic monomers, alicyclic monomers selected from the group consisting of cycloparrafins and cycloolefins, di-functional esters of phthalic acid, di-functional esters of methacrylic acid, multi-functional esters of acrylic acid, dienes, trienes, tetraenes, and N-methylene-Bis-acrylamide. Exemplary cross-linking monomers include divinylbenzene, trivinylbenzene, 1,2,4-tricinylcyclohexane, 1,5-hexadiene, 1,5,9-decatriene, 1,9-decadiene, and 1,5-heptadiene, di-allyl phthalate, ethylene glycol dimethacrylate, polyethylene glycol dimethacrylate, penta- and tetra-acrylates, and N-methylene-Bis-acrylamide. The polyethylene glycol dimethacrylates are particularly preferred for thickening in acid aqueous compositions, as they tend to minimize turbidity.

In certain preferred embodiments, an associative monomer may be used to prepare the rheology modifiers, in amounts up to about 30 weight percent, based on total weight of monomer. When used, the associative monomers preferably are used at levels ranging from about 0.1 to about 10 weight percent, based on total weight of monomer. Such monomers include those disclosed in U.S. Pat. Nos. 3,657,175, 4,384,096, 4,616,074, 4,743,698, 4,792,343, 5,011,978, 5,102,936, 5,294,692, and U.S. Pat. No. Re. 33,156, the contents of all which are hereby incorporated herein as if set forth in their entirety. Preferred associative monomers include the urethane reaction products of a monoethylenically unsaturated isocyanate and non-ionic surfactants comprising $C_1$–$C_4$ alkoxy-terminated, block copolymers of 1,2-butylene oxide and 1,2-ethylene oxide, as disclosed in U.S. Pat. No. 5,294,692 (Barron et al.), an ethylenically unsaturated copolymerizable surfactant monomer obtained by condensing a nonionic surfactant with methylenesuccinic acid (also known as itaconic acid) as disclosed in U.S. Pat. No. 4,616,074 (Ruffner), a surfactant monomer selected from the urea reaction product of a monoethylenically unsaturated monoisocyanate with a nonionic surfactant having amine functionality as disclosed in U.S. Pat. No. 5,011,978 (Barron et al.), and a nonionic urethane monomer which is the urethane reaction product of a monohydric nonionic surfactant with a monoethylenically unsaturated monoisocyanate, preferably one lacking ester groups such as alpha, alpha-dimethyl-m-iso-propenyl benzyl isocyanate as disclosed in U.S. Pat. No. Re. 33,156 (Shay et al.). Particularly preferred are the ethylenically unsaturated copolymerizable surfactant monomers obtained by condensing a non-ionic surfactant with methylenesuccinic acid. Methods for preparing such monomers are disclosed in detail in the various patents incorporated herein above.

The rheology modifier is prepared first by forming an emulsion utilizing single-stage emulsion polymerization techniques. Monomer, water, free-radical initiator, a first surfactant in amounts effective to disperse the polymer in the water upon polymerization of the monomers, and from about 0.5 to about 20 weight percent of an alcohol selected from the group consisting of a $C_2$–$C_{12}$ linear or branched monohydric alcohol and a non-polymeric polyhydric alcohol, such as ethylene glycol, propylene glycol and glycerol, based on total weight of the emulsion, are combined in a polymerization reactor and maintained at a desired temperature and for a period of time which are effective to polymerize the monomers, thereby forming a polymeric emulsion comprising the copolymer of monomers (a) and (b), water, surfactant and alcohol.

The contents of the polymerization vessel preferably are maintained at a temperature and for a period of time effective to cause polymerization of the monomers. Preferably the polymerization reaction is initiated at about 30 degrees Centigrade, with the contents of the polymerization vessel attaining a temperature of about 60 degrees Centigrade. The reaction time will be from about 1 to about 6 hours. One skilled in the art of emulsion polymerization will be able to ascertain readily exactly what conditions of temperature and time are required, as both are well within the knowledge of one skilled in the art.

Preferably, from about 1 to about 10 weight percent of the alcohol are used and, more preferably, from about 1 to about 5 weight percent of the alcohol are used, based on the total weight of the emulsion. If no alcohol, or an insufficient amounts of the alcohol, is used in preparing the emulsion, the resultant emulsion will not be stable to change in viscosity over time. It is desirable to minimize the level of alcohol used. The maximum amount of alcohol used may be limited practically by factors such as cost, flammability and volatile organic compound environmental concerns. Other than those factors, amounts of alcohol in excess of 20 weight percent conceivably may used.

It is essential that polymeric colloidal stabilizers such as polyvinyl alcohol not be used during preparation of the emulsion via emulsion polymerization in any amount which materially alters the properties of the emulsion, particularly the emulsion stability. Preferably, no polymeric colloidal stabilizer is used during emulsion preparation. It was discovered surprisingly that use of such polymeric colloidal stabilizers results in emulsions which are not stable to changes in viscosity or phase separation over time. Accordingly, the emulsions and rheology modifiers comprising the emulsions essentially are free and more preferably are free of polymeric colloidal stabilizers.

Thickened aqueous compositions according to the present invention, in addition to containing a thickening amount of the acrylate-based, stable aqueous emulsion, that is, an amount effective to thicken the aqueous composition compared to a comparable composition which does not contain the acrylate-based emulsion, will also comprise a minimum effective amount of an active ingredient selected from the group consisting of an acid and a second surfactant. Preferably, the thickened composition will comprise enough of the emulsion such that the thickened composition comprises greater than about 0.5 dry weight percent of the emulsion polymer on a dry weight basis, based on total weight of the thickened aqueous composition, and more preferably from about 0.5 to about 20 dry weight percent of the polymer, based on total weight of the thickened composition. Most preferably, the thickened composition will comprise from about 1 to about 10 dry weight percent of the emulsion polymer, based on total weight of the thickened composition.

By minimum effective amount, it is meant that the active ingredient will be present in the thickened aqueous composition in a minimum amount effective to provide the thickened aqueous composition with the particular performance characteristics required for the particular end-use of the thickened composition. For example, where the thickened composition is a cleanser, the composition must provide cleaning performance, as described below. In some cases, the surfactant may be used to enhance the thickening efficiency of the acrylate-based emulsion, for instance in an ink paste base or in an acid-containing cleanser. Accordingly, the thickened composition may comprise from about 0.1 to about 95 active weight percent of surfactant and/or from about 0.1 to about 50 active weight percent acid, based on total weight of the thickened composition, with the balance being polymer and water, as well as possibly other optional conventional ingredients utilized in thickened compositions described herein.

The actual active ingredient and the actual minimum effective amount will be determined by the actual product/application in which the thickened composition is to be used. For example, where the end-use is a cleaning composition such as a toilet bowl cleaner, a hard surface cleaner or a liquid hand dishwashing detergent, the active ingredient is selected from the group consisting of an acid and a second surfactant, present at a minimum amount effective to achieve minimum cleansing performance. By minimum cleansing performance, it is meant that the active ingredient is present in minimum amounts effective to clean or remove deposits from the surface of substrates to which the thickened aqueous compositions have been applied. For example, where the composition is applied to toilet bowls, an acid will be present in minimum amounts effective to remove salts and stains caused by continuous and/or repeated exposure to water, for example iron salts such as rust and the like. In this case, the thickened composition may comprise from about 0.1 to about 50 active weight percent of the acid, more preferably from about 2 to about 50 active weight percent of acid, based on total weight of the thickened composition. Where the compositions are applied in the form of a liquid hand dishwashing detergent to, for instance, dishes and plates, a second surfactant will be present in minimum amounts effective to remove deposits such as oils and fatty substances emanating from food products, dried food products themselves, dirt, and so forth. Preferably, such cleaning composition will comprise from about 2 to about 95 active weight percent of the second surfactant, more preferably from about 5 to about 95 active weight percent of the second surfactant, based on total weight of the thickened aqueous composition.

Exemplary acids used in compositions of the present invention include, without limitation, citric, sulfuric, hydrochloric, phosphoric, acetic, hydroxyacetic, and sulfamic acids. Synergistic thickening of compositions comprising an amount of an acid required for a desired performance have been surprisingly noted where a second surfactant selected from the group consisting of a nonionic and anionic surfactant is added to the composition. In those cases, the addition of the second surfactant has been found to improve thickening efficiency by as much as eighty fold, depending on the amount of surfactant added to the aqueous composition which comprises an acid. In these cases, the second surfactant need not be present at a level greater than that necessary to impart synergistic thickenening of the composition, as the acid performs the primary application function and the second surfactant serves to improve the thickening efficiency of the acrylate-based emulsion.

Thickened aqueous compositions according to the invention also include those compositions which comprise a second surfactant in minimum cleansing amounts. Such thickened compositions include, for example, liquid hand dishwashing detergents. Exemplary second surfactants which may be used in the thickened aqueous compositions include, without limitation, sodium lauryl sulfate, (di) alkylsulfosuccinates, alkyl sulfonates, alkyl phosphates, alkyl ethoxylates, and alkylaryl ethoxylates. It should be noted that the second surfactant is in addition to the first surfactant, which will be present in the aqueous composition due to its presence in the acrylate-based emulsion. Accordingly, the second surfactant may be formulated or blended into the aqueous composition after the emulsion has been prepared, and should not be confused with the first surfactant. While the second surfactant may be the same as the first surfactant, it is preferred that the second surfactant be selected from the group consisting of anionic and nonionic surfactants, and thus may be different than the first surfactant used to prepare the emulsion.

In addition to the above essential elements of the invention, the thickened aqueous compositions may further comprise conventional ingredients known to be used therein.

The following examples are set forth merely to exemplify the invention and are not intended to limit the metes and bounds of the invention, which is set forth by the claims appended hereto.

EXAMPLE 1

Acid Thickening

Two emulsions were prepared according to procedures set forth herein above and designated Emulsions 1A and 1B respectively. Each emulsion was prepared at twenty (20) weight percent polymer solids, based on total weight of the emulsion, utilizing acrylate-ester and alkylamino (meth) acrylate monomers. Each emulsion was incorporated into an acid-containing solution at a level such that the polymer solids, based on total weight of the thickened composition, are as set forth in Table 1.

TABLE 1

| Emulsion sample[2] | pH | Brookfield Viscosity[1] (cPs) | | | |
| --- | --- | --- | --- | --- | --- |
| | | initial | 1 day | 5 day | 35 day |
| Emulsion IA (20% polymer solids) | 8.2 | 50 | 60 | 66 | 92 |
| 3% 1A in 5% citric acid | 2.2 | 3200 | 6000 | 6000 | 5300 |
| 3% 1A in 5% hydroxyacetic/5% sulfamic acid blend | 2.2 | 2200 | 4500 | 4000 | 4400 |
| 4% 1A in 9% hydrochloric acid | 0.4 | 740 | 2060 | 1900 | — |

TABLE 1-continued

| Emulsion sample[2] | pH | Brookfield Viscosity[1] (cPs) | | | |
|---|---|---|---|---|---|
| | | initial | 1 day | 5 day | 35 day |
| Emulsion 1B (20% polymer solids) | 8.2 | 108 | 280 | 310 | 1550 |
| 3% 1B in 5% citric acid | 2.2 | 6000 | 8000 | 8700 | 8550 |
| 3% 1B in 5% hydroxyacetic/5% sulfamic acid blend | 2.3 | 4150 | 7000 | 6800 | 6800 |

[1]Brookfield viscometer model RVDVII+; All measurements obtained with spindle #2 @ 20 rpm, 21° C.
[2]All values are listed in dry weight % on total composition weight; e.g. 3% 1A polymer solids and 5% citric acid solids, based on total weight of thickened composition.

EXAMPLE 2

Surfactant Thickening

Stable emulsion 1A was added at the noted polymer solids to a blend of anionic and nonionic surfactants (2(a)) typical of commercially available liquid hand dishwashing detergents. The pH and Brookfield viscosity of the surfactant blend were recorded both prior to and after addition of the stable emulsion. The surfactant composition pH was then adjusted with addition of 50% sodium hydroxide solution to a pH 10 and the resulting Brookfield viscosity was recorded Again, the stable emulsion product unexpectedly provided a significant increase in the viscosity of the surfactant blend at pH 8.4 as well as pH 10.

Additional samples of anionic and non-ionic surfactants were selected for investigation of the ability of the stable emulsion thickener representative of this invention to thicken aqueous compositions comprising a second surfactant as the active ingredient. It is significant to note that the compositions of this example contain no acidic components, and no acid substances are added as neutralizing agents, compatibilizers, stablizers, or the like. The data contained in TABLE 2 includes as-is viscosity and pH measurements for an anionic surfactant (sodium lauryl sulfate, 2(d)) and a non-ionic surfactant (nonylphenol 4 mole ethoxylate (2(f)). The table also provides the resulting viscosity and pH of the referenced surfactant samples after addition of a noted level of the stable emulsion thickener 1A of this invention, demonstrating the ability of the stable emulsion thickener to provide an unexpected and substantial increase in the surfactant viscosity at an alkaline pH.

TABLE 2

| Sample # | Description | pH | Brookfield Viscosity[2] (cPs) |
|---|---|---|---|
| 2(a) | Commercial Anionic/Nonionic surfactant blend | 8.2 | 540 |
| 2(b) | Sample 2(a) with 1.2% Emulsion 1A added[1] | 8.4 | 1270 |
| 2(c) | Sample 2(b) with added sodium hydroxide | 10.0 | 930 |
| 2(d) | Sodium lauryl sulfate (30% active in water) | 8.6 | 94 |
| 2(e) | Sample 2(d) with 1.25% 1A emulsion added[1] | 9.3 | 738 |
| 2(f) | Nonylphenol ethoxylate | 9.3 | 386 |
| 2(g) | Sample 2(f) with 2.2% 1A emulsion added[1] | 8.1 | 1060 |

[1]dry polymer weight % on total composition weight;
[2]spindle #2 @ 20 rpm, 21° C.

EXAMPLE 3

Thickening Surfactant Containing Acidic Systems

Evaluation of the interaction of the stable emulsion product in an acidic system containing surfactant provided the data in TABLE 3, below. A solution containing 5 active weight % of citric acid was prepared. Addition of the stable emulsion product at a level of 2% dry polymer on total solution weight yielded a significant increase in the citric acid solution Brookfield viscosity. To the thickened acid solution was added, in 2 gram increments, an ethoxylated alkylphenol surfactant (HLB 8.8). Viscosity response to the incremental addition of the nonionic surfactant was recorded and demonstrates the ability of the stable emulsion product to thicken systems containing both acid and surfactant. Increasing the HLB of the added surfactant over the surfactant referenced in TABLE 3 is expected to provide an initial increase in the system viscosity that will more rapidly decrease with continued addition of the surfactant versus the referenced TABLE 3 viscosity data.

TABLE 3

| Sample # | Sample Description | Brookfield Viscosity (cPs)[1] |
|---|---|---|
| 3(a) | 5% Citric acid[2] solution | <10 |
| 3(b) | 3(a) + 2% 1A emulsion[2] | 216 |
| 3(c) | 3(b) + 2 grams nonionic surfactant | 4460 |
| 3(d) | 3(b) + 4 grams nonionic surfactant | 6200 |
| 3(e) | 3(b) + 6 grams nonionic surfactant | 8000 |
| 3(f) | 3(b) + 8 grams nonionic surfactant | 11200 |
| 3(g) | 3(b) + 10 grams nonionic surfactant | 16000 |
| 3(h) | 3(b) + 12 grams nonionic surfactant | 16000 |
| 3(i) | 3(b) + 14 grams nonionic surfactant | 9500 |
| 3(j) | 3(b) + 16 grams nonionic surfactant | 7200 |
| 3(k) | 3(b) + 18 grams nonionic surfactant | 6110 |
| 3(l) | 3(b) + 20 grams nonionic surfactant | 5000 |

[1]Brookfield Viscometer model RVDVII+; All measurements obtained with spindle #2 @ 20 rpm, 21° C.
[2]Solids weight percent based on total weight of solution.

We claim:

1. An aqueous detergent composition having a pH of less than or equal to about 11, comprising:
   a thickening amount of a stable emulsion of a polymer, said emulsion prepared by single-stage emulsion polymerization of monomers consisting of
   from about 5 to about 80 weight percent of an acrylate monomer (a) selected from the group consisting of a $C_2$–$C_6$ alkyl ester of acrylic acid and a $C_1$–$C_6$ alkyl ester of methacrylic acid,
   from about 5 to about 80 weight percent of a monomer (b) selected from the group consisting of a vinyl-substituted heterocyclic compound containing at least one of a nitrogen or sulfur atom, (meth)acrylamide, a mono- or di-($C_1$–$C_4$)alkylamino ($C_1$–$C_4$)alkyl (meth)acrylate, and a mono or di-($C_1$–$C_4$)alkylamino ($C_1$–$C_4$) alkyl (meth)acrylamide, and
   0.1 to about 30 weight percent of an associative monomer (d) wherein the percentage of monomers is based on 100 weight percent, wherein said emulsion polymerization is conducted in the presence of water, a first surfactant in amounts effective to emulsify the polymer in the water, a free-radical initiator and from about 0.5 to about 20 weight percent of an alcohol selected from the group consisting of a $C_2$–$C_{12}$ linear or branched monohydric alcohol and a non-polymeric polyhydric alcohol, based on the total weight of said emulsion, wherein said single-stage emulsion polymerization is conducted in the absence of a polymeric colloidal stabilizer; and a minimum effective amount of an active ingredient selected from the group consisting of an acid and a second surfactant.

2. The composition of claim 1 wherein said emulsion comprises from about 15 to about 40 weight percent of said polymer, based on the total weight of said emulsion.

3. The composition of claim 1 wherein said emulsion comprises from about 0.1 to about 5 weight percent of said first surfactant, based on the total weight of monomer, said first surfactant selected from the group consisting of anionic, cationic, nonionic, amphoteric and zwitterionic surfactants.

4. The composition of claim 1 wherein said associative monomer is selected from the group consisting of urethane reaction products of a monoethylenically unsaturated isocyanate and nonionic surfactants comprising $C_1$–$C_4$ alkoxy-terminated, block copolymers of 1,2-butylene oxide and 1,2-ethylene oxide, an ethylenically unsaturated copolymerizable surfactant monomer obtained by condensing a nonionic surfactant with methylene succinic acid, a surfactant monomer selected from the a group consisting of a urea reaction product of a monoethylenically unsaturated monoisocyanate with a nonionic surfactant having amine functionality, and a nonionic urethane monomer which is the urethane reaction product of a monohydric nonionic surfactant with a monoethylenically unsaturated isocyanate.

5. The composition of claim 1 wherein the monomer (b) is selected from the group consisting of N,N-dimethylamino ethyl methacrylate, N,N-diethylamino ethyl acrylate, N,N-diethylamino ethyl methacrylate, N-t-butylamino ethyl acrylate, N-t-butylamino ethyl methacrylate, N,N-dimethylamino propyl acrylamide, N,N-dimethylamino propyl methacrylamide, N,N-diethylamino propyl acrylamide and N,N-diethylamino propyl methacrylamide.

6. The composition of claim 1 wherein said second surfactant is selected from the group consisting of anionic and nonionic surfactants.

7. The composition of claim 1 comprising from about 2 to about 50 weight percent of said acid, based on the total weight of said composition.

8. The composition of claim 1 comprising from about 0.1 to about 50 weight percent of said acid, based on the total weight of said composition.

9. The composition of claim 1 comprising from about 0.5 to about 20 dry weight percent of said polymer, based on total weight of said composition.

10. The composition of claim 1 wherein said acid is selected from the group consisting of citric, sulfuric, hydrochloric, phosphoric, acetic, hydroxyacetic and sulfamic acids.

11. The composition of claim 1 wherein said second surfactant is selected from the group consisting of sodium lauryl sulfate, (di)alkylsulfosuccinates, alkyl sulfonates, alkyl phosphates, alkyl ethoxylates and alkylaryl ethoxylates.

* * * * *